United States Patent
Palafox, Sr.

(10) Patent No.: US 6,743,827 B1
(45) Date of Patent: *Jun. 1, 2004

(54) METHOD FOR PREPARING COLLOIDAL SOLUTION OF BISMUTH SODIUM TARTRATE

(76) Inventor: Fernando Palafox, Sr., 4304 O'Keefe St., El Paso, TX (US) 79902

(*) Notice: Subject to any disclaimer, the term of this patent is extended or adjusted under 35 U.S.C. 154(b) by 0 days.

This patent is subject to a terminal disclaimer.

(21) Appl. No.: 10/265,818

(22) Filed: Oct. 7, 2002

Related U.S. Application Data

(63) Continuation of application No. 09/547,704, filed on Apr. 12, 2000, now Pat. No. 6,482,865.

(51) Int. Cl.[7] .................. B01F 3/12; A61K 31/191; C07F 9/94
(52) U.S. Cl. .................. 516/77; 514/574; 514/819; 556/77; 556/79
(58) Field of Search .................. 516/77; 556/77, 556/79; 562/585; 514/574, 819

(56) References Cited

U.S. PATENT DOCUMENTS

| | | | | |
|---|---|---|---|---|
| 1,540,117 A | * | 6/1925 | Giemsa | |
| 1,663,201 A | | 3/1928 | Kober | |
| 1,906,666 A | | 5/1933 | Torigian | .......... 556/77 X |
| 4,965,382 A | | 10/1990 | Furlan | .......... 556/79 |
| 5,399,356 A | | 3/1995 | Chapura et al. | .......... 424/451 |
| 6,482,865 B1 | * | 11/2002 | Palafox, Sr. | .......... 516/77 |

* cited by examiner

*Primary Examiner*—Daniel S. Metzmaier
(74) *Attorney, Agent, or Firm*—Loeffler Jonas & Tuggey LLP

(57) ABSTRACT

A method for preparation of a semitransparent colloidal solution of bismuth sodium tartrate generally comprises producing an aqueous solution of bismuth sodium tartrate; extracting a magma of bismuth sodium tartrate from the aqueous solution at a pH of approximately 2.2; and then dissolving the magma into a salting-in mixture. After addition of preservative and strength testing, the base solution is diluted to elixir strength. The elixir is then buffered to a pH range of about 7.2 to about 7.3 in order to maintain for an extended duration the semitransparent nature of the elixir.

21 Claims, 3 Drawing Sheets

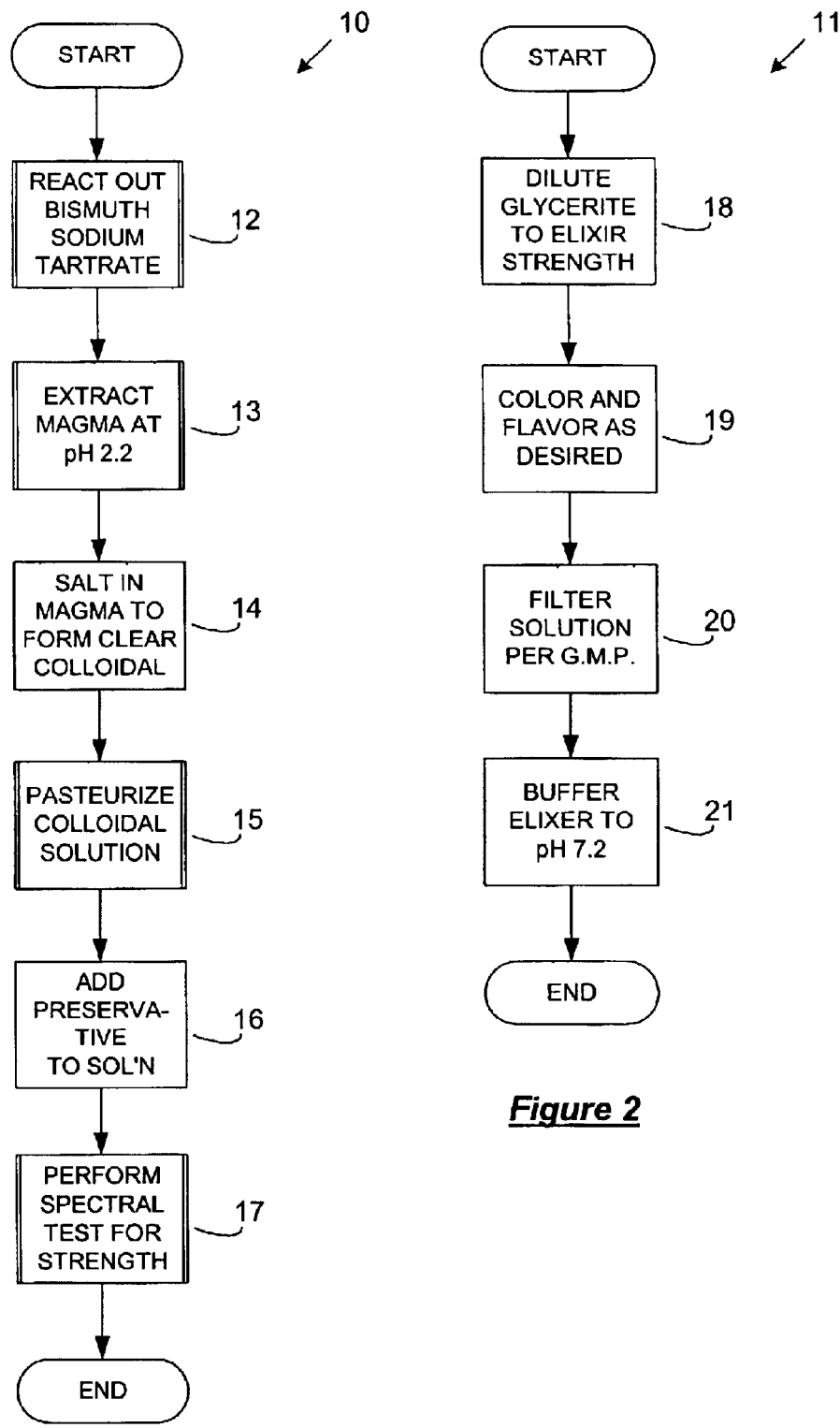

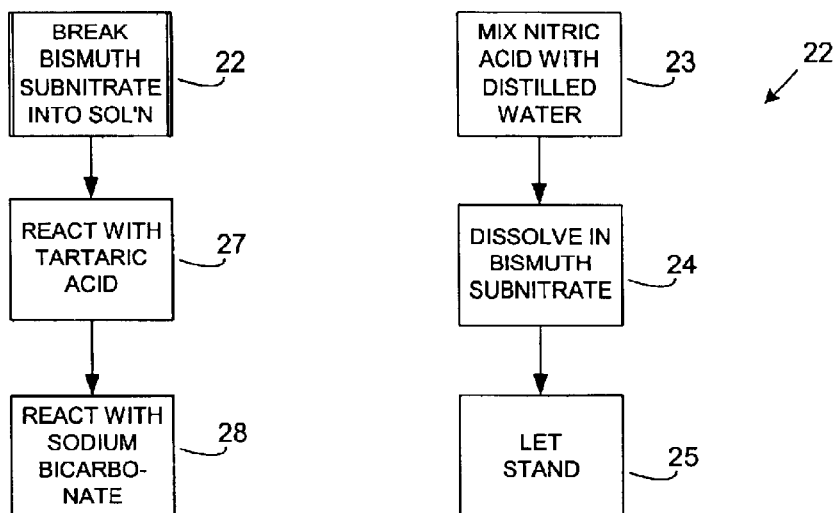
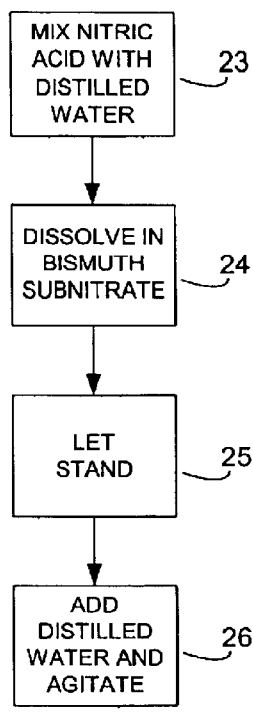
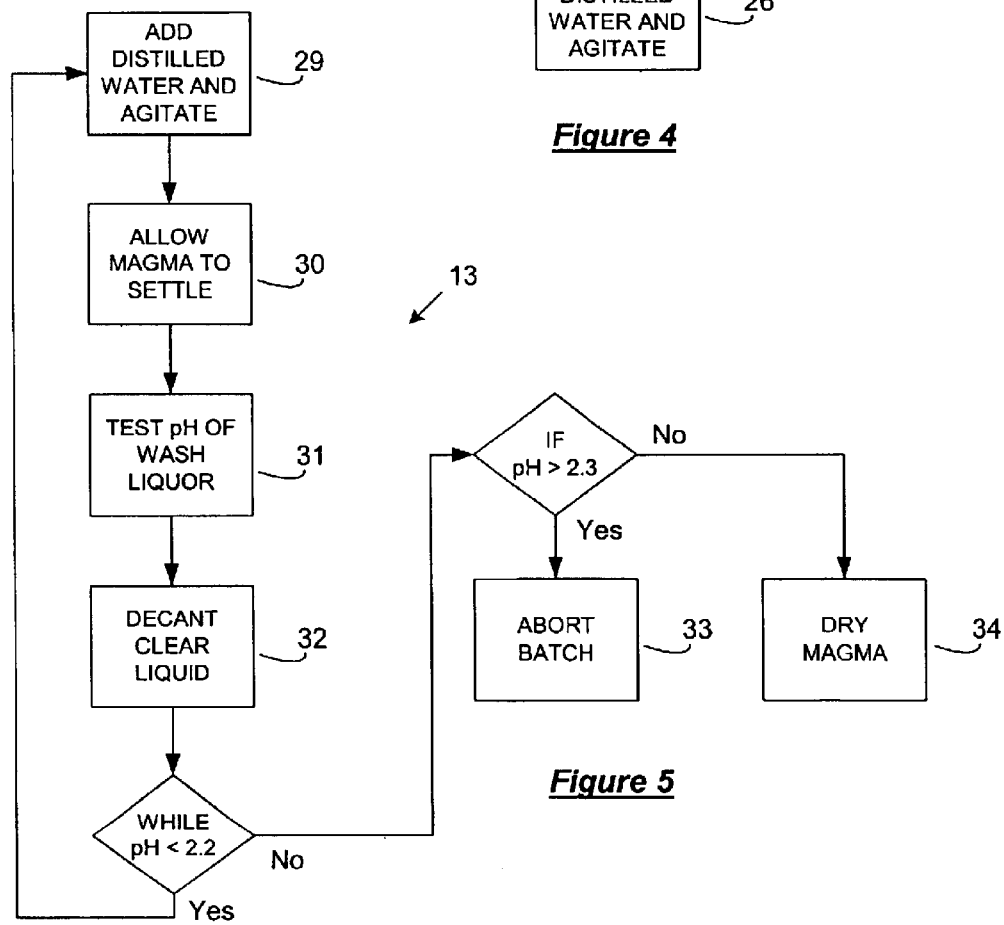
*Figure 3*
*Figure 4*
*Figure 5*

METHOD FOR PREPARING COLLOIDAL SOLUTION OF BISMUTH SODIUM TARTRATE

RELATED APPLICATION

The present application is a continuation, under 35 U.S.C. § 120, of U.S. patent application Ser. No. 09/547,704 filed Apr. 12, 2000, which issued as U.S. Pat. No. 6,482,865 B1 on Nov. 19, 2002, which is incorporated herein by reference.

FIELD OF THE INVENTION

The present invention relates to the preparation of colloidal solutions. More particularly, the invention relates to a method for the preparation of a semitransparent colloidal solution of bismuth sodium tartrate with an extended, stable shelf life.

BACKGROUND OF THE INVENTION

Elixir of bismuth has been known at least since the 1936 National Formulary for treatment of various maladies of the gastrointestinal tract, including acid indigestion. According to the 1936 National Formulary, elixir of bismuth is produced by diluting a quantity of glycerite of bismuth and adding further quantities of glycerin and aromatic elixirs as preservative agents. The glycerite of bismuth, as produced according to the 1936 National Formulary, generally comprises a milky colloidal solution of bismuth sodium tartrate.

Unfortunately, the National Formulary has failed to provide an accurate method for testing the strength of the glycerite of bismuth and has also failed to suggest methodologies for elimination of aromatic elixirs. As a result, the elixir of bismuth has to date been difficult and unnecessarily expensive to produce in desired strength.

It is therefore an overriding object of the present invention to improve over the methods of the prior art by presenting a method whereby bismuth sodium tartrate may be produced in a semitransparent colloidal solution, which solution may be accurately and safely tested for strength of active ingredient. It is a further object of the present invention to present such a method wherein the resulting elixir may be expected to have an extended shelf life. Finally, it is yet another object of the present invention to present such a method wherein regulated ingredients, such as aromatic elixirs, may be eliminated from the formula without compromise of product integrity.

SUMMARY OF THE INVENTION

In accordance with the foregoing objects, the present invention—a method for preparation of a semitransparent colloidal solution of bismuth sodium tartrate—generally comprises the steps of producing an aqueous solution of bismuth sodium tartrate; extracting a magma of bismuth sodium tartrate from the aqueous solution at a pH of approximately 2.2; and then dissolving the magma into a salting-in mixture to form the semitransparent colloidal solution of bismuth sodium tartrate. It is critical to the present invention that the magma be extracted at a pH of at least 2.2 but not more than 2.3. As a result, in the preferred method of the present invention, the magma is extracted by washing with a wash liquor comprising an addition of distilled water; allowing the magma to settle out of the wash liquor; measuring the pH of the wash liquor after the magma has settled; and then decanting the wash liquor from the magma. This process is then repeated as necessary to arrive at a magma within the critical pH range, whereafter the magma is air dried in preparation for salting-in.

In the preferred method of the present invention, the salting-in solution is prepared by heating a quantity of distilled water; dissolving a quantity of sodium bicarbonate into the heated quantity of distilled water; and then mixing a quantity of tartaric acid with the solution of sodium bicarbonate and heated distilled water. In this manner, freezing of the salting-in solution is prevented, thereby ensuring a proper mixture.

The preferred method of the present invention further comprises the step of pasteurizing the semitransparent colloidal solution of bismuth sodium tartrate in order to eliminate the need for aromatic elixirs without compromise of product purity. In order to prevent damage to the active ingredient, however, the pasteurizing step comprises raising the semitransparent colloidal solution of bismuth sodium tartrate to a temperature of approximately 54.5° C.; holding the solution at the pasteurization temperature for at least five but not more than eight minutes; and then returning the solution to ambient temperature.

The resulting semitransparent solution may then be tested for strength utilizing spectral methods. In at least one implementation of the present invention, this may comprise the steps of measuring a quantity of light transmitted through a sample of the semitransparent colloidal solution of bismuth sodium tartrate; converting the measured quantity of light to an indicium of the density of active ingredient present within the solution; and then calculating the per unit quantity of bismuth trioxide present.

The preferred method of the present invention also comprises diluting the base solution to an elixir strength according to the tested strength of the base. It is critical, however, that the dilute elixir be buffered to a critical pH range in order to sustain prolonged shelf life without degradation of the semitransparent nature of the product. In particular, sodium bicarbonate is added to the end product to achieve a final pH of about 7.2 to 7.3.

Finally, many other features, objects and advantages of the present invention will be apparent to those of ordinary skill in the relevant arts, especially in light of the foregoing discussions and the following drawings, exemplary detailed description and appended claims.

BRIEF DESCRIPTION OF THE DRAWINGS

Although the scope of the present invention is much broader than any particular embodiment, a detailed description of the preferred embodiment follows together with illustrative figures, wherein like reference numerals refer to like components, and wherein:

FIG. 1 shows, in flowchart, the first phase of manufacture according to the preferred method of the present invention of a semitransparent colloidal solution of bismuth sodium tartrate;

FIG. 2 shows, in flowchart, the second phase of manufacture according to the preferred method of the present invention of a semitransparent colloidal solution of bismuth sodium tartrate;

FIG. 3 shows, in flowchart, details of the production of an aqueous solution of bismuth sodium tartrate as implemented according to the steps of FIG. 1;

FIG. 4, shows, in flowchart, details of a step in the production of the aqueous solution described in FIG. 3;

FIG. 5 shows, in flowchart, details of the magma extraction process as implemented according to the steps of FIG. 1;

DETAILED DESCRIPTION OF THE PREFERRED EMBODIMENT

Figure 6:
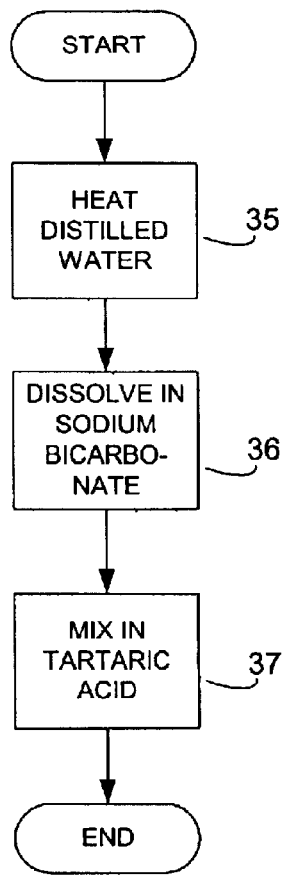
FIG. 6 shows, in flowchart, a preferred method for production of a salting-in solution utilized according to the steps of FIG. 1.

Although those of ordinary skill in the art will readily recognize many alternative embodiments, especially in light of the illustrations provided herein, this detailed description is exemplary of the preferred embodiment of the present invention, the scope of which is limited only by the claims appended hereto.

As shown in the accompanying Figures, a semitransparent colloidal solution of bismuth sodium tartrate is preferably formed in two distinct manufacturing processes—the preparation of a base comprising a glycerite of bismuth 10, as particularly shown in FIG. 1, and, thereafter, the dilution of the base to an elixir of bismuth 11, as particularly shown in FIG. 2. In the first phase 10 of manufacture, a glycerite of bismuth is generally prepared by producing an aqueous solution of bismuth sodium tartrate 12, extracting a magma of bismuth sodium tartrate from the aqueous solution 13 and then dissolving the magma into a salting-in mixture 14 to initially form the semitransparent colloidal solution of bismuth sodium tartrate. The resultant base is then preferably pasteurized 15, for reasons that will be better understood further herein, after which a preservative of glycerin may be added 16. Because the solution obtained according to the method described herein is semitransparent, spectral techniques may be readily employed to safely test the base for strength 17 after which it may be placed in bulk storage until such time as an elixir strength may be desired. In the second phase 11 of manufacture, the base formula is diluted to elixir strength 18, according to the tested strength of active ingredient, and then prepared for consumer packaging 19, 20, 21.

Although those of ordinary skill in the art will recognize the adjustments necessary to produce other quantities of solutions, especially in light of this exemplary description, the following description specifies the quantities necessary for production of approximately 12 gallons of a base of glycerite of bismuth with a strength of 130 mg/ml bismuth trioxide. As will be apparent to those of ordinary skill in the art, this quantity is sufficient to yield approximately 100 gallons elixir of bismuth. Although those of ordinary skill in the art will also recognize that the relative quantities of active and/or reactive ingredients are critical to the successful conduct of the present invention, the absolute values are of course typically not critical.

Referring now to FIG. 3, the preferred method for producing the aqueous solution of bismuth sodium tartrate from bismuth subnitrate 12—a known starting material for the active ingredient—is detailed. In the first step, 8.16 kg of bismuth subnitrate is broken into solution in order that further chemical reactions may be effected 22. As known to those of ordinary skill in the art, and as detailed in FIG. 4, this may be accomplished by mixing 7.24 liters of nitric acid with 11.35 liters of distilled water 23 and dissolving the bismuth subnitrate therein 24. After a standing period of approximately 15 minutes to allow operation of the acidic solution on the bismuth subnitrate 25, a further quantity of 26.5 liters of distilled water is added to dilute the volatile solution to a more safely manageable mixture. At this point, the solution is agitated to ensure complete breakdown of the bismuth subnitrate 26. Referring now again to FIG. 3, the broken down solution of bismuth subnitrate is then reacted with 7.03 kg of tartaric acid NF to form bismuth tartrate 27. Finally, 9.75 kg of sodium bicarbonate USP is added, in small quantities to prevent violent reaction, to the solution of bismuth tartrate to form the desired aqueous solution of bismuth sodium tartrate 28. Although the foregoing method is the recognized standard procedure for preparation of bismuth sodium tartrate in an aqueous solution, those of ordinary skill in the art will recognize many possible alternatives. For example, it may be possible to break down the bismuth subnitrate with acids other than the very powerful nitric acid. In any case, all such substantially equivalent methods should be considered within the scope of the present invention.

In the next steps of manufacture, as shown in FIG. 1, a magma of bismuth sodium tartrate is extracted from the aqueous solution 13 and then dissolved into a salting-in solution to initially form a colloidal solution of bismuth sodium tartrate 14. Although it is known that the magma of bismuth sodium tartrate must be washed in order to raise its pH to a level safe for handling and fit for consumption, it is critical to the present invention that the magma of bismuth sodium tartrate be extracted from the aqueous solution at a pH of approximately 2.2 but not greater than approximately 2.3 in order for the magma to remain soluble. Applicant has discovered that extraction of the magma at a pH greater than 2.3 will result in eventual breakdown of the magma—clouding the semitransparent colloidal solution and in turn preventing the application of spectral techniques for strength testing and generally resulting in a less attractive product for human consumption.

Referring now to FIG. 5, the preferred method for extracting the magma at the desired pH 13 is detailed. As shown in the Figure, distilled water is added to the aqueous solution of bismuth sodium tartrate after which the solution is agitated to wash the magma 29. The magma is then allowed to settle 30 at which time the pH of the wash liquor is tested 31. The wash liquor is then decanted from the magma 32 and, so long as the pH remains below about 2.2, this process is repeated for the further elimination of the strong acid remaining therein. In the event the magma is over-washed, as indicated by a measured pH greater than 2.3, the batch must be aborted 33 and the entire manufacturing process restarted. As a consequence, in order to ensure no product loss, those of ordinary skill in the art will recognize the necessity for strict process control during this phase, including careful adjustment of the quantity of distilled water added to the wash. Finally, once the desired pH of between about 2.2 and about 2.3 is obtained, the properly extracted magma is drained and allowed to dry in preparation for salting-in 34.

As shown in FIG. 6, the salting-in solution comprises a mixture of sodium bicarbonate USP and tartaric acid NF. Because the chemical reaction of sodium bicarbonate with tartaric acid causes a dramatic temperature drop, Applicant has found it desirable to preheat a sodium bicarbonate solution prior to the introduction thereto of the tartaric acid. In this manner freezing of the solution is prevented and a complete and proper chemical reaction is ensured. In particular, Applicant has found success in raising 11.35 liters of distilled water to approximately 38° C. in a fifteen gallon stainless steel tank 35. Upon reaching this temperature, 5.44 kg of sodium bicarbonate USP is mixed with the water until completely dissolved 36 whereafter 4.64 kg of tartaric acid NF is added, thereby effecting a clear salting-in solution 37. The dry or slightly moist magma of bismuth sodium tartrate may then be dissolved into the properly reacted salting-in solution 14. Provided that the magma was extracted at the specified pH and that a properly proportioned salting-in solution has been effected, the magma will completely dissolve into the salting-in solution to form a substantially clear, yellowish colloidal solution of bismuth sodium tartrate.

Figure 7:
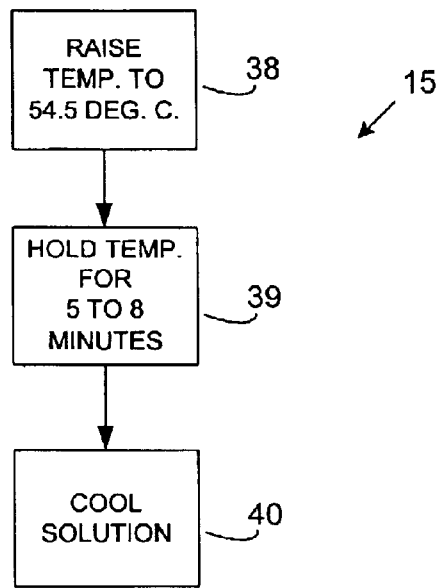
FIG. 7 shows, in flowchart, details of a pasteurization process as implemented according to the steps of FIG. 1.

Because Applicant has found that it is desirable to eliminate aromatic elixirs high in alcohol content in order to reduce government regulation as well as to provide a more palatable and less likely contraindicated product for human consumption, Applicant has introduced a pasteurization step 15 in the production of the base solution 10. As a result, the cost of production is dramatically reduced through the elimination of regulatory reporting as well as the ability to use less than chemically pure tartaric acid. Applicant has found, however, that the pasteurization must be carefully effected in order to ensure purification of the tartaric acid—particularly the killing of any yeast contaminant—without damage to the end product as may result from cooking of the sodium bicarbonate. As shown in FIG. 7, the preferred method for pasteurization 15 of the semitransparent colloidal solution comprises raising the temperature of the solution to approximately 54.5° C. 38, holding the solution at the pasteurization temperature for at least five but not more than eight minutes 39, and thereafter cooling the solution to ambient temperature 40. After the solution is cooled, glycerin q.s. to 45.4 liters is added as a preservative 16.

Figure 8:
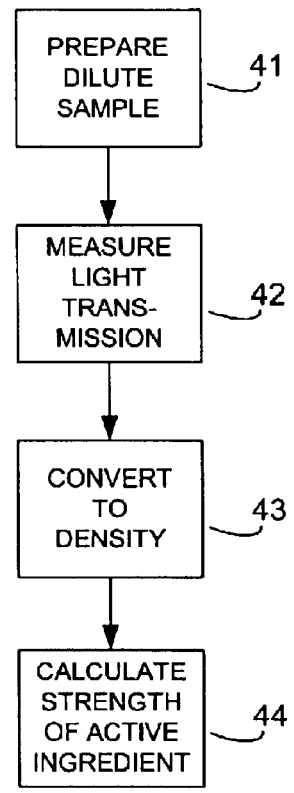
FIG. 8 shows, in flowchart, details of spectral strength test as implemented according to the steps of FIG. 1.

One particular benefit of producing bismuth sodium tartrate in a semitransparent colloidal solution is that such a solution is particularly adapted for strength testing by spectral methods. As described in FIG. 8, such a spectral method may comprise the preparation of a dilute sample 41 through which a light transmission is measured 42. As is known to those of ordinary skill in the art, the measured light transmission can then be converted to a density value based upon calibration tables for the particular spectral instrument being used 43. The resulting density value may then be used to calculate the strength of the active ingredient 44—in the present case bismuth trioxide, which strength may be used in the second phase 11 of manufacture to effect an accurate dilution of the glycerite of bismuth to an elixir of bismuth 18.

Referring now again to FIG. 2, it is preferred that the glycerite of bismuth be diluted to elixir strength when finally packaged for distribution to consumers. The dilution is effected, as known to those of ordinary skill in the art, in order to obtain the specified dosage of active ingredient by volume according to the tested strength of the base 18. Coloring and/or flavoring agents may then be added as desired 19. According to the preferred method of the present invention, the solution is then filtered in accordance with good manufacturing practices to ensure elimination of any foreign object as may have been introduced in the manufacture or storage of the base solution 20.

Finally, Applicant has found that it is critical to package the elixir of bismuth at a pH of at least 7.2 but not more than 7.3 in order to obtain significant shelf life without degeneration of the semitransparent colloidal solution. Although it is generally known that the pH should be neutral or higher to avoid exacerbation of the medical indication for which the product is used, a pH of approximately 7.3 has been empirically discovered as an upper limit of this rule of thumb. Buffering the end product to a pH above the critical range will result in the formation over time of undesirable precipitates within the solution. Because this will result in a product generally unsuitable for ordinary consumer markets, care should be observed in obtaining the desired end pH. According to the preferred method of manufacture, the end pH is obtained by adding sodium bicarbonate USP as necessary to arrive at the critical range 21.

While foregoing description is exemplary of the preferred embodiment of the present invention, those of ordinary skill in the relevant arts will recognize the many variations, alterations, modifications, substitutions and the like as are readily possible, especially in light of this description, the accompanying drawings and claims drawn thereto. In any case, because the scope of the present invention is much broader than any particular embodiment, the foregoing detailed description should not be construed as a limitation of the scope of the present invention, which is limited only by the claims appended hereto.

What is claimed is:

1. A method for preparing a semitransparent colloidal solution of bismuth sodium tartrate, said method comprising the steps of:

producing an aqueous solution of bismuth sodium tartrate;

extracting a magma of bismuth sodium tartrate from said aqueous solution, said magma having a pH of approximately 2.2;

dissolving said magma into a salting-in mixture to form said semitransparent colloidal solution of bismuth sodium tartrate; and diluting said semitransparent colloidal solution of bismuth sodium tartrate to an elixir strength.

2. The method as recited in claim 1, wherein said magma is extracted from said aqueous solution at a pH of at least 2.2 but not more than 2.3.

3. The method as recited in claim 1, said method further comprising the step of buffering said elixir strength semitransparent colloidal solution of bismuth sodium tartrate to a pH of at least 7.2 but not more than 7.3.

4. The method as recited in claim 3, wherein said magma is extracted from said aqueous solution at a pH of at least 2.2 but not more than 2.3.

5. The method as recited in claim 3, wherein said buffering step comprises the addition of a quantity of sodium bicarbonate to said elixir strength semitransparent colloidal solution of bismuth sodium tartrate.

6. A method for preparing a semitransparent colloidal solution of bismuth sodium tartrate, said method comprising the steps of:

producing an aqueous solution of bismuth sodium tartrate;

extracting a magma of bismuth sodium tartrate from said aqueous solution, said magma having a pH of approximately 2.2;

dissolving said magma into a salting-in mixture to form said semitransparent colloidal solution of bismuth sodium tartrate; and testing said semitransparent colloidal solution of bismuth sodium tartrate for strength of bismuth trioxide.

7. The method as recited in claim 6, wherein said magma is extracted from said aqueous solution at a pH of at least 2.2 but not more than 2.3.

8. The method as recited in claim 6, said method further comprising the step of diluting said semitransparent colloidal solution of bismuth sodium tartrate to an elixir strength.

9. The method as recited in claim 8, wherein said magma is extracted from said aqueous solution at a pH of at least 2.2 but not more than 2.3.

10. The method as recited in claim 8, said method further comprising the step of buffering said elixir strength semitransparent colloidal solution of bismuth sodium tartrate to a pH of at least 7.2 but not more than 7.3.

11. The method as recited in claim 10, wherein said magma is extracted from said aqueous solution at a pH of at least 2.2 but not more than 2.3.

12. The method as recited in claim 10, wherein said buffering step comprises the addition of a quantity of sodium bicarbonate to said elixir strength semitransparent colloidal solution of bismuth sodium tartrate.

13. The method as recited in claim 10, wherein said testing step comprises performing a spectral analysis of said semitransparent colloidal solution of bismuth sodium tartrate.

14. The method as recited in claim 13, wherein said performing a spectral analysis step comprises the steps of:
   measuring a quantity of light transmitted through a sample of said semitransparent colloidal solution of bismuth sodium tartrate;
   converting said measured quantity of light to an indicium of the density of active ingredient present within said semitransparent colloidal solution of bismuth sodium tartrate; and
   calculating the per unit quantity of bismuth trioxide present within said semitransparent colloidal solution of bismuth sodium tartrate according to said indicium.

15. The method as recited in claim 8, wherein said testing step comprises performing a spectral analysis of said semitransparent colloidal solution of bismuth sodium tartrate.

16. The method as recited in claim 15, wherein said performing a spectral analysis step comprises the steps of:
   measuring a quantity of light transmitted through a sample of said semitransparent colloidal solution of bismuth sodium tartrate;
   converting said measured quantity of light to an indicium of the density of active ingredient present within said semitransparent colloidal solution of bismuth sodium tartrate; and
   calculating the per unit quantity of bismuth trioxide present within said semitransparent colloidal solution of bismuth sodium tartrate according to said indicium.

17. The method as recited in claim 6, wherein said testing step comprises performing a spectral analysis of said semitransparent colloidal solution of bismuth sodium tartrate.

18. The method as recited in claim 17, wherein said magma is extracted from said aqueous solution at a pH of at least 2.2 but not more than 2.3.

19. The method as recited in claim 17, wherein said performing a spectral analysis step comprises the steps of:
   measuring a quantity of light transmitted through a sample of said semitransparent colloidal solution of bismuth sodium tartrate;
   converting said measured quantity of light to an indicium of the density of active ingredient present within said semitransparent colloidal solution of bismuth sodium tartrate; and
   calculating the per unit quantity of bismuth trioxide present within said semitransparent colloidal solution of bismuth sodium tartrate according to said indicium.

20. A method for preparing a semitransparent colloidal solution of bismuth sodium tartrate, said method comprising the steps of:
   producing an aqueous solution of bismuth sodium tartrate;
   extracting a magma of bismuth sodium tartrate from said aqueous solution at a pH of at least 2.2 but not more than 2.3 by:
     washing said magma with a wash liquor, said wash liquor comprising an addition of distilled water,
     settling said magma out of said wash liquor;
     measuring the pH of said wash liquor after said settling said magma step; and
     decanting said wash liquor from said magma;
   dissolving said magma into a salting-in mixture to form said semitransparent colloidal solution of bismuth sodium tartrate;
   pasteurizing said semitransparent colloidal solution of bismuth sodium tartrate;
   adding a preservative to said semitransparent colloidal solution of bismuth sodium tartrate;
   testing said semitransparent colloidal solution of bismuth sodium tartrate for strength of bismuth trioxide by performing a spectral analysis of said semitransparent colloidal solution of bismuth sodium tartrate;
   diluting said semitransparent colloidal solution of bismuth sodium tartrate to an elixir strength; and
   buffering said elixir strength semitransparent colloidal solution of bismuth sodium tartrate to a pH of at least 7.2 but not more than 7.3.

21. The method as recited in claim 20, wherein said buffering step comprises the addition of a quantity of sodium bicarbonate to said elixir strength semitransparent colloidal solution of bismuth sodium tartrate.

* * * * *